United States Patent [19]

Eide et al.

[11] 4,004,457
[45] Jan. 25, 1977

[54] COMPRESSION TESTER

[75] Inventors: Richard Eide, Minneapolis; Gerald A. Golembeck, Lake Elmo, both of Minn.

[73] Assignee: The United States Bedding Company, St. Paul, Minn.

[22] Filed: Jan. 13, 1976

[21] Appl. No.: 648,768

[52] U.S. Cl. .................................................. 73/94
[51] Int. Cl.² ......................................... G01N 3/08
[58] Field of Search .......................... 73/94, 78, 81

[56] References Cited

UNITED STATES PATENTS

| | | | |
|---|---|---|---|
| 2,041,869 | 5/1936 | Smith et al. | 73/94 |
| 2,049,644 | 8/1936 | Essen | 73/94 |
| 2,376,814 | 5/1945 | Robinson | 73/94 |
| 2,703,492 | 3/1955 | Brissette et al. | 73/94 |

*Primary Examiner*—James J. Gill
*Assistant Examiner*—Anthony V. Ciarlante
*Attorney, Agent, or Firm*—McDougall, Hersh & Scott

[57] ABSTRACT

A compression tester for resilient objects such as springs and foam articles, including a supporting bed for the object to be tested. A platen is positioned on the object and a driving handle is engaged for forcing the platen into the object. A scale measures the amount of force applied and the distance of movement of the platen into the object is simultaneously indicated. This provides a tester which will determine the force required for depressing a resilient object through a given distance.

6 Claims, 8 Drawing Figures

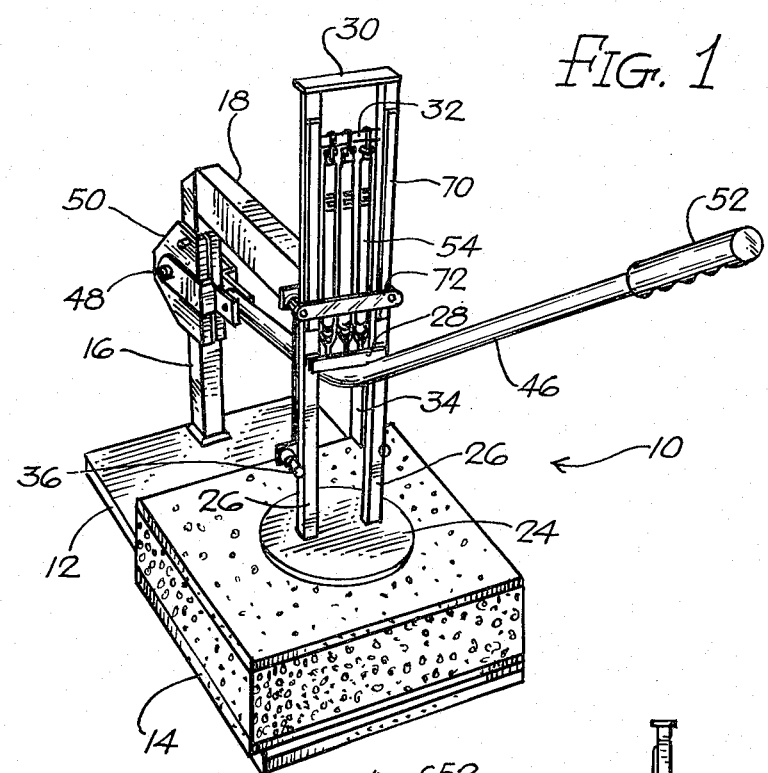
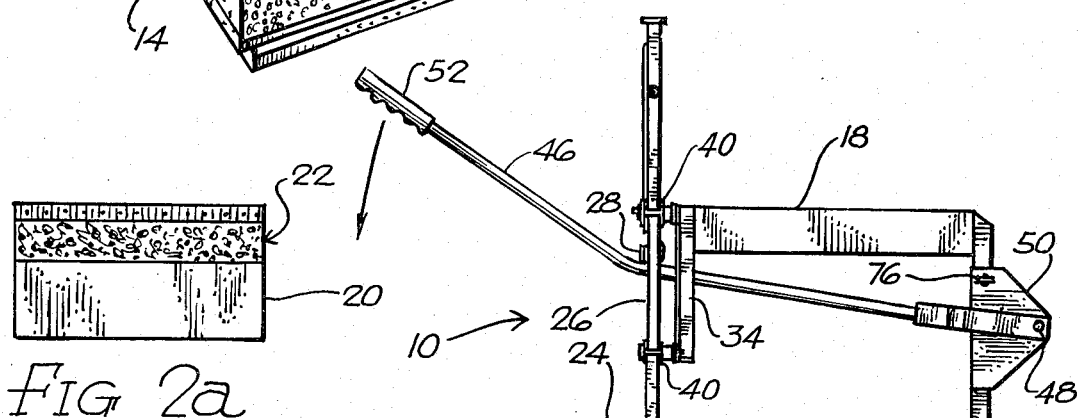
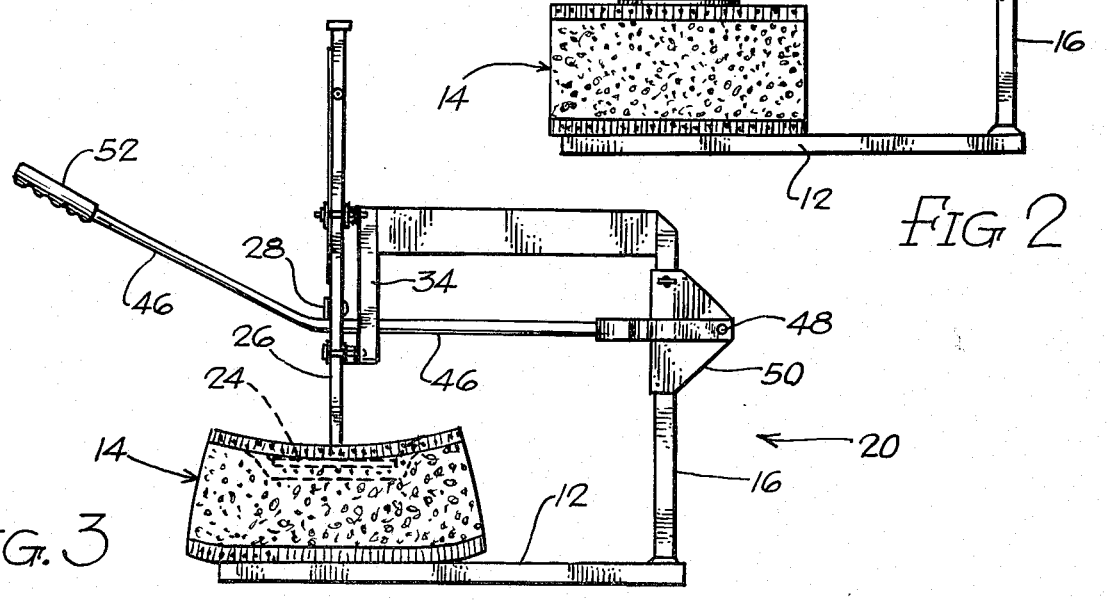
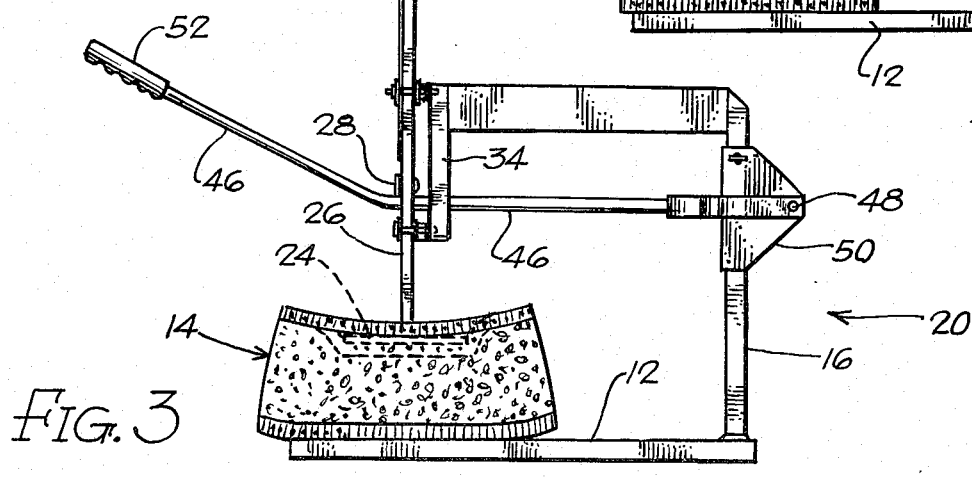

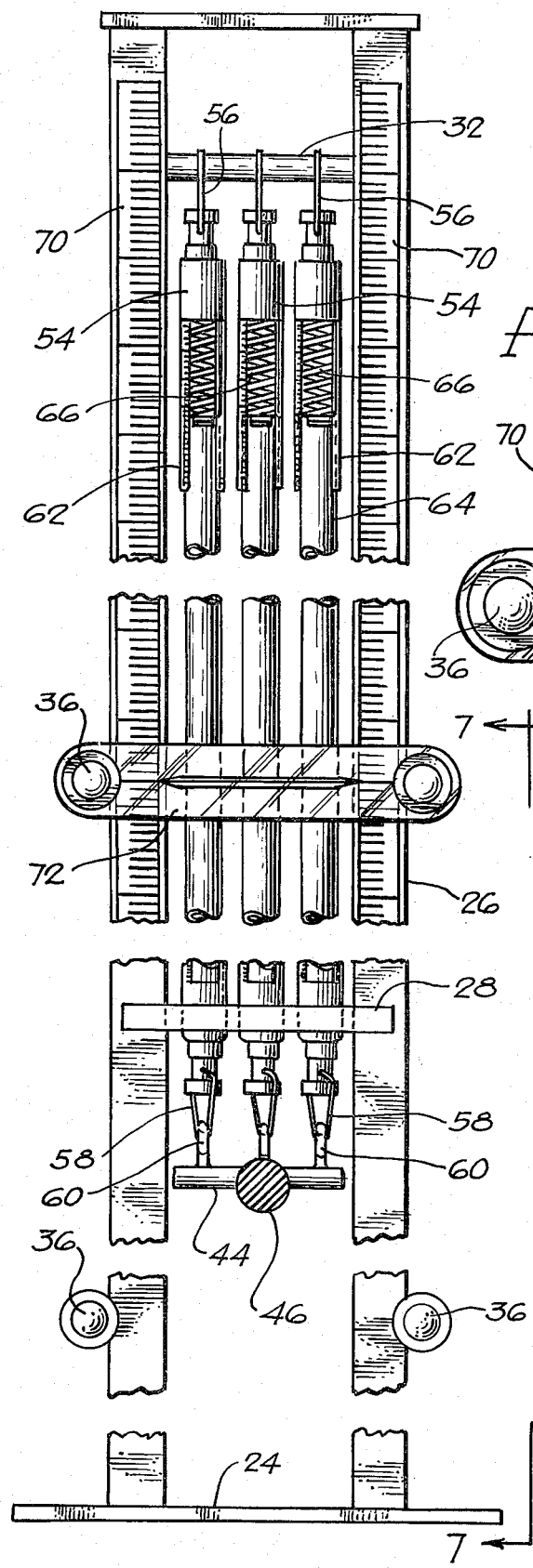
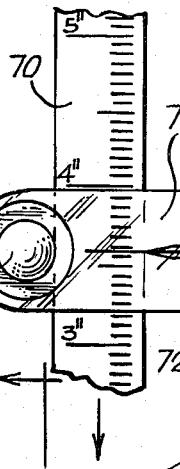
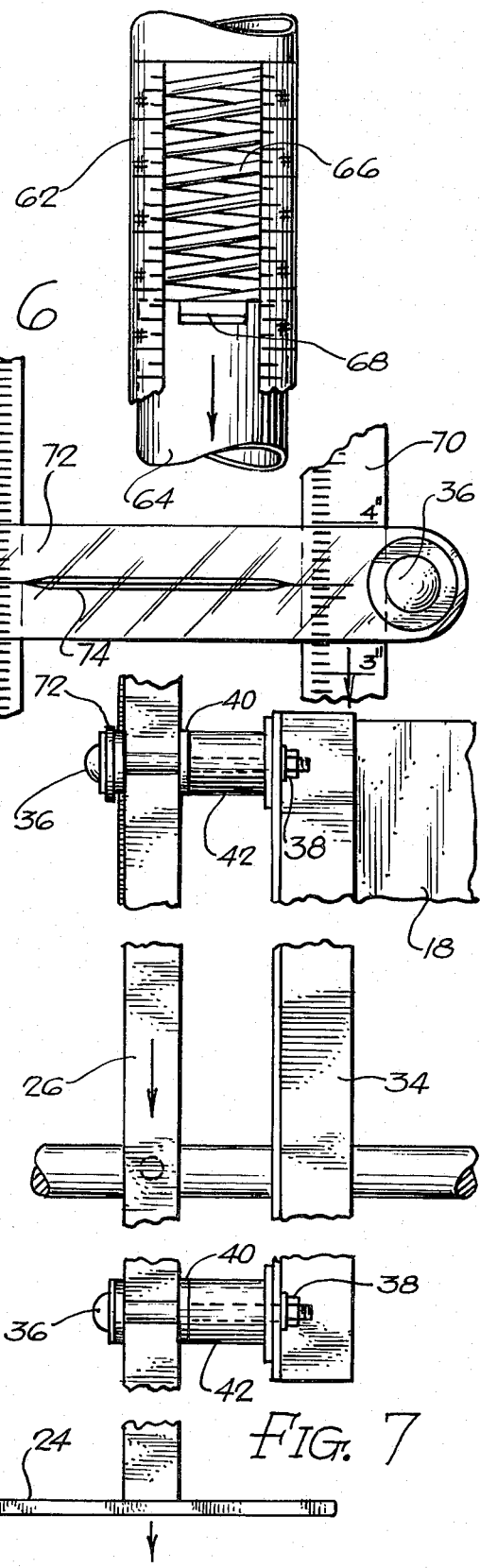

COMPRESSION TESTER

This invention relates to a compression tester. The invention is particularly concerned with a compression tester capable of determining the compression force necessary for deflecting springs, spring assemblies, foam samples, composites of foam and springs, and other resilient objects including completed cushions and mattresses.

Objects of the type referred to above are tested for various reasons. Testing is typically conducted on cushions and mattresses or on springs or spring assemblies utilized in such mattresses for purposes of providing a comfort evaluation. The testing results also provide a means for quality control and evaluation of materials and products.

In terms of the force applied during testing, attempts are made to simulate the weight of individuals who would be likely to use such objects. Deflection measurements are useful for determining the ability of cushions and mattresses to remain reasonably flat or firm for individuals of a given weight. Testing of other resilient objects would be conducted along essentially the same lines.

It is a general object of this invention to provide a compression tester which is relatively straightforward in design and which can be efficiently manufactured and used to provide a broad range of compression testing capability.

It is a more specific object of this invention to provide a compression tester which is portable and which is completely self-contained so that it can be employed with a great deal of ease and efficiency.

It is a further specific object of this invention to provide a compression tester which has relatively few operating parts and which is uncomplicated in operation whereby the maintenance and use of the tester is greatly simplified.

These and other objects of this invention will appear hereinafter, and for purposes of illustration, but not of limitation, a specific embodiment of the invention is illustrated in the accompanying drawings in which:

FIG. 1 is a perspective view of a compression tester characterized by the features of this invention;

FIG. 2 is a side view of the compression tester;

FIG. 2a is an illustration of an adapter which can be employed in conjunction with the compression tester;

FIG. 3 is a side view of the compression tester with force applied to a resilient object;

FIG. 4 is an enlarged fragmentary front elevation of a compression tester;

FIG. 5 is an enlarged fragmentary view illustrating a scale portion utilized in the compression tester;

FIG. 6 is an enlarged fragmentary sectional view illustrating frame portions which enable deflection measurements; and, FIG. 7 is a fragmentary side view taken about the line 7—7 of FIG. 4.

This invention generally relates to a compression tester for resilient objects. The tester includes a supporting bed for an object to be tested and a platen is movably positioned over the bed. Means are provided for driving the platen into the object and measuring means are utilized for determining the force applied to the platen.

The platen is mounted on a movable frame and means are provided for determining the distance of movement of the frame and the platen. Accordingly, the user of the tester can determine both the force applied and the amount of depression of the platen into the object being tested. This then provides a means for determining the properties of the object being tested and the properties provide data for evaluating the object. "Indentation load deflection (ILD)", "hysteresis loss" and "creep" tests are typical examples of evaluations which can be undertaken with the construction of the invention.

The accompanying drawings illustrate a compression tester 10 characterized by the features of the invention. This tester includes a horizontal bed portion 12 which is provided for supporting the object 14 being tested. The drawings illustrate a foam object. However, as indicated, several different types of resilient objects can be tested and the following description is applicable to the testing of such other objects.

A vertically extending post 16 is supported on the bed and a horizontally extending beam 18 is connected at the upper end of this post. The beam extends in spaced relationship relative to the bed 12, and this relationship generally determines the thickness of objects which can be tested with the construction. Thus, objects of the thickness of mattresses are typical of the objects which can be tested with the construction, and the size of the tester 10 will be determined accordingly. On the other hand, larger or smaller testing units employing the operating principles of this invention are also contemplated.

Objects of smaller size can be tested through the utilization of the arrangement shown in FIG. 2a. In this instance an adapter block 20 is utilized for supporting a thinner resilient object 22. The adapter block is positioned on the bed 12 and is incompressible so that a determination of the amount of deflection of the object 22 can be accurately made.

The platen 24 is utilized for achieving the deflection or depression into the object being tested. This platen is mounted on the bottom end of vertically extending frame members 26. The frame members are held together by means of an intermediate crossbrace 28 and an upper crossbrace 30. In addition, a suspending bar 32 extends between the frame members 26 and assists in rigidifying the frame.

The horizontal beam 18 supports a pair of downwardly extending angle members 34. As best shown in FIGS. 4 and 7, bolts 36 are attached to the angle members 34 by means of nuts 38. Guide spools 40 are positioned by means of spacer tubes 42 around the shaft of the bolt, and these spools serve as guide members for the frame members 26.

The frame members 26 comprise square tubes and the laterally extending bar 44 shown in FIG. 4 is positioned between these tubes.

The bar 44 extends through the arm 46. This arm is pivotally connected at 48 to a bracket 50 which is supported by the vertically extending post 16. The handle 52 at the opposite end of the arm is employed for pivoting the arm and for applying force during operation of the construction as will be more fully explained.

The suspending bar 32 is employed for supporting scales 54. As best shown in FIG. 4, each of these scales includes a loop 56 at its upper end which connects the scales to the bar 32. Additional loops 58 at the lower ends of the scales are utilized for securing the scales to hooks 60 formed on the pin 44.

The scales 54 are of the type including an outer cylinder 62 which is held stationary relative to the bar 32. Each scale includes an inner cylinder 64 and each has a spring 66 connected at its upper end to the outer cylinder and at its lower end to the inner cylinder. It will be appreciated that with this arrangement each scale operates upon movement of the inner cylinder relative to the outer cylinder, this movement being resisted by the force of a spring 66. Upon proper calibration, the force applied to a given scale can be measured by determining the relative movement of the cylinders.

FIG. 5 illustrates in greater detail the relationship between the outer cylinder 62 and inner cylinder 64 of a scale. Gradations are provided on the outer cylinder and an indicator tab 68 which is part of the inner cylinder provides a convenient means for reading the relative positons of the cylinders.

A pair of rulers 70 are secured to the frame members 26 as best shown in FIGS. 4 and 6. A transparent strip 72 is associated with the beam 18 by means of the upper set of bolts 36, and this strip includes a reference line 74. Since the rulers can be seen through the strip 72, readings which will indicate movement between the frame members and the strip are made possible.

The bracket 50 which is attached to the vertical post 16 is adapted to be adjusted relative to the post. For this purpose a pin 76 extends through an opening in the bracket and into one of several spaced openings (not shown) in the post 16. The bracket can thus be raised and lowered which will, of course, affect the position of the arm 46.

In the operation of the tester, it is desired to have the arm 46 disposed substantially horizontally over the bed 12 during the test in the manner shown in FIG. 3. Accordingly, the first step in the operation is preferably the adjustment of the bracket 50. It is also contemplated that the platen 24 could be adjustable relative to the frame members 26 or capable of swiveling to achieve a flat relationship with respect to the upper surface of the object being tested.

The tester is operated by pulling downwardly on the handle 52 which will result in the movement of the platen into the object 14 as shown in FIG. 3. The force applied to the handle is transmitted through pin 44 to the scales 54 and then through the scales to the frame supporting the platen. The amount of force is measured in pounds applied to the platen of standardized area, usually 50 square inches. In this connection the gradations on the outer cylinder 62 are such that a force reading is directly taken from the scale. It should also be noted that where three scales are employed in the manner illustrated then the sum of the three readings must be utilized. It will be appreciated that the scales are removable, and that a single scale or two or more scales could readily be employed.

The application of some force will necessarily result in at least some movement of the frame members 26. The user of the device must, therefore, determine the position of the frame members relative to the reference line on the transparent member 72 before the force is applied. A reading is then taken after force is applied to determine the amount of deflection of the platen into the object. This figure is then taken into consideration along with the force reading.

For certain tests, including ASTM D1564 and RMA Buyer's Specification — Latex Foam, the element of time is also a factor. Accordingly, the operator must also determine the time involved in achieving the application of a certain force or the obtaining of a certain deflection. This is, of course, a simple determinaton.

In a typical construction of the type described, the unit 10 will be about 30 inches high and weigh about 45 pounds, which makes it portable for convenient and efficient use. Scales 54 of 50-pound capacity may be utilized which will enable the application of up to 150 pounds of force. Where lesser force application is involved, one or two of the scales may be removed. The platen 24 wll typically have an engaging surface area in the order of 50 square inches.

The structure may include different rulers 70 such as a standard scale and a ¾ ruler conventionally used to make 25 percent deflection ILD tests. A structure of the type described will readily handle objects of 4 to 8 inches in thickness. Thicker objects may be tested by suitably modifying the construction, and thinner objects can be tested utilizing the adapter block.

It will be understood that various changes and modifications may be made in the above described construction which provide the characteristics of the invention without departing from the spirit thereof, particularly as defined in the following claims.

That which is claimed is:

1. In a compression tester for resilient objects comprising a supporting bed for the object to be tested, a platen movably positioned over said supporting bed, a movable frame supporting said platen, a scale for measuring the force applied by said platen to said object, an actuating arm for driving the platen into said object, said scale having an upper end suspended from said frame and a lower end connected to said actuating arm, driving force applied to said actuating arm being transmitted through said arm to said scale, and through said scale to said frame and platen whereby driving of the platen into said object provides a reading on said scale for determination of the force applied, and means for measuring the distance of depression of the platen into the object whereby the force required for depression of the platen for a given distance can be measured.

2. An apparatus in accordance with claim 1 including graduations displayed on said frame, an indicator connected to the supporting means for said object, said indicator being positioned adjacent said graduations whereby the graduations on said frame move relative to said indicator thereby providing a measure of the distance of depression of said platen.

3. An apparatus in accordance with claim 2 including a handle on one end of said actuating arm extending outwardly from one side of said frame, the opposite end of said arm extending outwardly from the frame on the other side thereof, and means pivotally connecting said opposite end to said supporting bed for said object.

4. An apparatus in accordance with claim 3 including means for adjusting said opposite end whereby said platen is adapted to be located in a substantially level position when engaging said object in the absence of force applied to the object.

5. An apparatus in accordance with claim 1 including an adapter block positioned on said supporting bed for said object, said adapter block supporting objects of lesser thickness for engagement by said platen.

6. An apparatus in accordance with claim 1 including three scales mounted in side-by-side relationship on said frame, and means for removing one or two of said scales for adjusting the capabilities of the tester.

* * * * *